(12) United States Patent
Bundy et al.

US012371751B2

(10) Patent No.: US 12,371,751 B2
(45) Date of Patent: Jul. 29, 2025

(54) PAPER-BASED COLORIMETRIC COVID-19/SARS-COV-2 TEST

(71) Applicant: Brigham Young University, Provo, UT (US)

(72) Inventors: Bradley C. Bundy, Provo, UT (US); J. Porter Hunt, Provo, UT (US)

( * ) Notice: Subject to any disclaimer, the term of this patent is extended or adjusted under 35 U.S.C. 154(b) by 621 days.

(21) Appl. No.: 17/319,845

(22) Filed: May 13, 2021

(65) Prior Publication Data

US 2021/0355552 A1 Nov. 18, 2021

Related U.S. Application Data

(60) Provisional application No. 63/024,295, filed on May 13, 2020.

(51) Int. Cl.
| | | |
|---|---|---|
| *C12Q 1/70* | (2006.01) | |
| *C07H 21/04* | (2006.01) | |
| *C12Q 1/6825* | (2018.01) | |

(52) U.S. Cl.
CPC .............. *C12Q 1/70* (2013.01); *C07H 21/04* (2013.01); *C12Q 1/6825* (2013.01)

(58) Field of Classification Search
None
See application file for complete search history.

(56) References Cited

U.S. PATENT DOCUMENTS

| | | |
|---|---|---|
| 2005/0053951 A1 | 3/2005 | Breaker et al. |
| 2016/0017342 A1 | 1/2016 | Valle et al. |
| 2016/0313255 A1 | 10/2016 | Pardee et al. |
| 2018/0334731 A1 | 11/2018 | Pardee et al. |
| 2019/0024192 A1 | 1/2019 | Kotula et al. |
| 2019/0218624 A1 | 7/2019 | Green et al. |
| 2019/0285620 A1 | 9/2019 | Green et al. |
| 2020/0071777 A1 | 3/2020 | Green et al. |
| 2020/0080137 A1 | 3/2020 | Green et al. |
| 2020/0318148 A1 | 10/2020 | Pardee et al. |

FOREIGN PATENT DOCUMENTS

| | | | | |
|---|---|---|---|---|
| WO | WO-9528942 A1 | * | 11/1995 | ............. C07H 21/00 |
| WO | 2017087530 A1 | | 5/2017 | |
| WO | 2018026762 A1 | | 2/2018 | |
| WO | 2019008133 A1 | | 1/2019 | |

OTHER PUBLICATIONS

Makami et al., Protein Expression and Purification, 2008, 62:190-198. (Year: 2008).*
Borujeni, A. E.; Salis, H. M., Translation Initiation is Controlled by RNA Folding Kinetics via a Ribosome Drafting Mechanism. J. Am. Chem. Soc. 2016, 138 (22), 7016-7023.
Brooks, S. K.; Webster, R. K.; Smith, L. E.; Woodland, L.; Wessely, S.; Greenberg, N.; Rubin, G. J., The psychological impact of quarantine and how to reduce it: rapid review of the evidence. Lancet 2020, 395 (10227), 912-920.
Bundy, B. C.; Franciszkowicz, M. J.; Swartz, J. R., *Escherichia coli*-based cell-free synthesis of virus-like particles. Biotechnol. Bioeng. 2008, 100 (1), 28-37.
Bundy, B. C.; Swartz, J. R., Efficient disulfide bond formation in virus-like particles. J. Biotechnol. 2011, 154 (4), 230-239.
"Chappell J, Watters KE, Takahashi MK, Lucks JB. A renaissance in RNA synthetic biology: new mechanisms, applications and tools for the future. Current opinion in chemical biology. Oct. 1, 2015;28:47-56."
Du, Z.; Giedroc, D. P.; Hoffman, D. W., Structure of the autoregulatory pseudoknot within the gene 32 messenger RNA of bacteriophages T2 and T6: a model for a possible family of structurally related RNA pseudoknots. Biochemistry 1996, 35 (13), 4187-98.
Hunt, J. P.; Wilding, K. M.; Barnett, R. J.; Robinson, H.; Soltani, M.; Cho, J. E.; Bundy, B. C., Engineering Cell-Free Protein Synthesis for High-Yield Production and Human Serum Activity Assessment of Asparaginase: Toward On-Demand Treatment of Acute Lymphoblastic Leukemia. Biotechnol. J. 2020, 15 (4), e1900294.
Fritz, B. R.; Jewett, M. C., The impact of transcriptional tuning on in vitro integrated rRNA transcription and ribosome construction. Nucleic Acids Res. 2014, 42 (10), 6774-6785.
Gandhi, M.; Yokoe, D. S.; Havlir, D. V., Asymptomatic Transmission, the Achilles' Heel of Current Strategies to Control Covid-19. N. Engl. J. Med. 2020.
Geraldi A, Giri-Rachman EA. Synthetic biology-based portable in vitro diagnostic platforms. Alexandria journal of medicine. 2018;54(4):423-8.
Green, A. A.; Silver, P. A.; Collins, J. J.; Yin, P., Toehold Switches: De-Novo-Designed Regulators of Gene Expression. Cell 2014, 159 (4), 925-939.
He, B.; Rong, M.; Lyakhov, D.; Gartenstein, H.; Diaz, G.; Castagna, R.; McAllister, W. T.; Durbin, R. K., Rapid mutagenesis and purification of phage RNA polymerases. Protein Expr. Purif. 1997, 9 (1), 142-51.
Henrich, E.; Hein, C.; Dotsch, V.; Bernhard, F., Membrane protein production in *Escherichia coli* cell-free lysates. FEBS Lett. 2015, 589 (15), 1713-22.
Hoang Trung Chau, T., Hoang Anh Mai, D., Ngoc Pham, D., Thi Quynh Le, H., & Yeol Lee, E. (2020). Developments of Riboswitches and Toehold Switches for Molecular Detection—Biosensing and Molecular Diagnostics. International Journal of Molecular Sciences, 21(9), 3192. doi:10.3390/ijms21093192.
International Search Report and Written Opinion for corresponding International Application No. PCT/US2021/032274, 11 pages (Sep. 21, 2021).
Isaacs, F. J.; Dwyer, D. J.; Ding, C.; Pervouchine, D. D.; Cantor, C. R.; Collins, J. J., Engineered riboregulators enable post-transcriptional control of gene expression. Nat. Biotechnol. 2004, 22 (7), 841-7.
Jiang, X. P.; Oohira, K.; Iwasaki, Y.; Nakano, H.; Ichihara, S.; Yamane, T., Reduction of protein degradation by use of protease-deficient mutants in cell-free protein synthesis system of *Escherichia coli*. J. Biosci. Bioeng. 2002, 93 (2), 151-156.

(Continued)

*Primary Examiner* — Nicole Kinsey White
(74) *Attorney, Agent, or Firm* — Ryan L. Marshall; Rachel E. Pricer; Barnes & Thornburg LLP (57) ABSTRACT

Disclosed herein are biosensors, which may be made from cell lysates, purified enzymes, or a combination thereof, for testing for the presence of a pathogen, such as SARS-CoV-2. The biosensor may be used in the context of a paper-based test, such as a colorimetric COVID-19 test. Methods of using the biosensor are also disclosed.

18 Claims, 6 Drawing Sheets

Specification includes a Sequence Listing.

(56) References Cited

OTHER PUBLICATIONS

Lo, I. L., Lio, C. F., Cheong, H. H., Lei, C. I., Cheong, T. H., Zhong, X., . . . Sin, N. N. (2020). Evaluation of SARS-CoV-2 RNA shedding in clinical specimens and clinical characteristics of 10 patients with COVID-19 in Macau. International Journal of Biological Sciences, 16(10), 1698-1707. doi:10.7150/ijbs.45357.

Ma, D.; Shen, L.; Wu, K.; Diehnelt, C. W.; Green, A. A., Low-cost detection of norovirus using paper-based cell-free systems and synbody-based viral enrichment. Synthetic Biology 2018, 3 (1).

Martz L. Paperback diagnostics. Science-Business exchange. Nov. 20, 2014;7(45):1310-.

Meyer, A. J.; Ellefson, J. W.; Ellington, A. D., Directed Evolution of a Panel of Orthogonal T7 RNA Polymerase Variants for in Vivo or in Vitro Synthetic Circuitry. ACS Synth. Biol. 2015, 4 (10), 1070-6.

Mutalik, V. K.; Qi, L.; Guimaraes, J. C.; Lucks, J. B.; Arkin, A. P., Rationally designed families of orthogonal RNA regulators of translation. Nat. Chem. Biol. 2012, 8 (5), 447-454.

Pardee, K.; Green, A. A.; Ferrante, T.; Cameron, D. E.; DaleyKeyser, A.; Yin, P.; Collins, J. J., Paper-based synthetic gene networks. Cell 2014, 159 (4), 940-54.

Pardee, K.; Green, A. A.; Takahashi, M. K.; Braff, D.; Lambert, G.; Lee, J. W.; Ferrante, T.; Ma, D.; Donghia, N.; Fan, M.; Daringer, N. M.; Bosch, I.; Dudley, D. M.; O'Connor, D. H.; Gehrke, L.; Collins, J. J., Rapid, Low-Cost Detection of Zika Virus Using Programmable Biomolecular Components. Cell 2016, 165 (5), 1255-66.

Plant, E. P.; Perez-Alvarado, G. C.; Jacobs, J. L.; Mukhopadhyay, B.; Hennig, M.; Dinman, J. D., A three-stemmed mRNA pseudoknot in the SARS coronavirus frameshift signal. PLoS Biol. 2005, 3 (6), e172- e172.

Qiu, J., Covert coronavirus infections could be seeding new outbreaks. Nature 2020.

Salehi, A. S. M.; Smith, M. T.; Bennett, A. M.; Williams, J. B.; Pitt, W. G.; Bundy, B. C., Cell-free protein synthesis of a cytotoxic cancer therapeutic: Onconase production and a just-add-water cell-free system. Biotechnol. J. 2016, 11 (2), 274-281.

Salehi, A. S. M.; Tang, M. J. S.; Smith, M. T.; Hunt, J. M.; Law, R. A.; Wood, D. W.; Bundy, B. C., Cell-Free Protein Synthesis Approach to Biosensing hTRp-Specific Endocrine Disruptors. Anal. Chem. 2017, 89 (6), 3395-3401.

Salehi, A. S. M.; Yang, S. O.; Earl, C. C.; Shakalli Tang, M. J.; Porter Hunt, J.; Smith, M. T.; Wood, D. W.; Bundy, B. C., Biosensing estrogenic endocrine disruptors in human blood and urine: A Rapid cell-free protein synthesis approach. Toxicol. Appl. Pharmacol. 2018, 345 (1096-0333 (Electronic)), 19-25.

Schinn, S.-M.; Bradley, W.; Groesbeck, A.; Wu, J. C.; Broadbent, A.; Bundy, B. C., Rapid In Vitro Screening for the Location-Dependent Effects of Unnatural Amino Acids on Protein Expression and Activity. Biotechnol. Bioeng. 2017, 114 (10), 2412-2417.

Shin, J.; Noireaux, V., An *E. coli* Cell-Free Expression Toolbox: Application to Synthetic Gene Circuits and Artificial Cells. ACS Synth. Biol. 2012, 1 (1), 29-41.

Shin, J.; Noireaux, V., Efficient cell-free expression with the endogenous *E. coli* RNA polymerase and sigma factor 70. J. Biol. Eng. 2010, 4, 8-8.

Smith, M. T.; Bennett, A. M.; Hunt, J. M.; Bundy, B. C., Creating a Completely "Cell-free" System for Protein Synthesis. Biotechnol. Prog. 2015, 31 (6), 1716-1719.

Smith, M. T.; Berkheimer, S. D.; Werner, C. J.; Bundy, B. C., Lyophilized *Escherichia coli*-based cell-free systems for robust, high-density, long-term storage. Biotechniques 2014, 56 (4), 186-193.

Smith, M. T.; Hawes, A. K.; Shrestha, P.; Rainsdon, J. M.; Wu, J. C.; Bundy, B. C., Alternative fermentation conditions for improved *Escherichia coli*-based cell-free protein synthesis for proteins requiring supplemental components for proper synthesis. Process Biochem. 2014, 49 (2), 217-222.

Smith, M. T.; Varner, C. T.; Bush, D. B.; Bundy, B. C., The incorporation of the A2 protein to produce novel Qb virus-like particles using cell-free protein synthesis. Biotechnol. Prog. 2012, 28 (2), 549-555.

Soltani, M.; Davis, B. R.; Ford, H.; Nelson, J. A. D.; Bundy, B. C., Reengineering Cell-Free Protein Synthesis as a Biosensor: Biosensing with Transcription, Translation, and Protein-folding. Biochem. Eng. J. 2018, 138, 165-171.

Staple, D. W.; Butcher, S. E., Pseudoknots: RNA structures with diverse functions. PLoS Biol. 2005, 3 (6), e213-e213.

Sutton, D.; Fuchs, K.; D'Alton, M.; Goffman, D., Universal Screening for SARS-CoV-2 in Women Admitted for Delivery. N. Engl. J. Med. 2020.

Takahashi, M. K.; Lucks, J. B., A modular strategy for engineering orthogonal chimeric RNA transcription regulators. Nucleic Acids Res. 2013, 41 (15), 7577-7588.

Wilding, K. M.; Hunt, J. P.; Wilkerson, J. W.; Funk, P. J.; Swensen, R. L.; Carver, W. C.; Christian, L. M., Endotoxin-free *E. coli*-based cell-free protein synthesis: Pre-expression endotoxin removal approaches for on-demand cancer therapeutic production. Biotechnol. J. 2018, 14 (3), 1800271.

Wu, J. C. Y.; Hutchings, C. H.; Lindsay, M. J.; Werner, C. J.; Bundy, B. C., Enhanced Enzyme Stability Through Site-Directed Covalent Immobilization. J. Biotechnol. 2015, 193, 83-90.

Zawada, J. F.; Yin, G.; Steiner, A. R.; Yang, J.; Naresh, A.; Roy, S. M.; Gold, D. S.; Heinsohn, H. G.; Murray, C. J., Microscale to Manufacturing Scale-up of Cell-Free Cytokine Production—A New Approach for Shortening Protein Production Development Timelines. Biotechnol. Bioeng. 2011, 108 (7), 1570-1578.

Medscape Covid-19 Infographic. https://www.medscape.com/slideshow/covid-19-infographics-6012689#1. Dated Mar. 31, 2020.

NIH. Clinical Trials Using Glutaminase Inhibitor CB-839. https://www.cancer.gov/about-cancer/treatment/clinical-trials/intervention/glutaminase-inhibitor-cb-839. Available at least as early as May 13, 2020.

Test for Current Infection. Center for Disease Control and Prevention. https://www.cdc.gov/coronavirus/2019-ncov/testing/diagnostic-testing.html. Available at least as early as May 13, 2020 ; Updated Jan. 5, 2022.

\* cited by examiner

SEQUENCE LISTING

<160> NUMBER OF SEQ ID NOS: 3

<210> SEQ ID NO 1

```
<211> LENGTH: 60
<212> TYPE: DNA
<213> ORGANISM: Artificial Sequence
<220> FEATURE:
<223> OTHER INFORMATION: Target sequence

<400> SEQUENCE: 1
ggagccttga atacaccaaa agatcacatt ggcacccgca atcctgctaa caatgctgca      60

<210> SEQ ID NO 2
<211> LENGTH: 395
<212> TYPE: DNA
<213> ORGANISM: Artificial Sequence
<220> FEATURE:
<223> OTHER INFORMATION: DNA for Pseudoknot

<400> SEQUENCE: 2
taatacgact cactataggt gcagcattgt tagcaggatt gcgggtgcca atgtgatctt      60
ttggtgtatt caaggctcct ttgtttaact ttaagaagga gacctgctaa caatgctgca     120
aggagccttg aatacaccaa tgaccatgat tacggattca ctggccgtcg ttttacaacg     180
tcgtgactgg gaaaaccctg gcgttaccca acttaatcgc cttgccgccc atccccttt      240 cgccagctgc gtaatagcg aagaggcccg caccgatcgc ccttcccaac agttgcgcag     300
cctgaatggc gaatggcgct ttgccgcggc cgcactcgag taagcaacta gcataacccc     360
ttggggcctc taaacgggtc ttgaggggtt ttttg                                395

<210> SEQ ID NO 3
<211> LENGTH: 395
<212> TYPE: RNA
<213> ORGANISM: Artificial Sequence
<220> FEATURE:
<223> OTHER INFORMATION: RNA sequence of pseudoknot

<400> SEQUENCE: 3
uaauacgacu cacuauaggu gcagcauugu uagcaggauu gcgggugcca augugaucuu      60 uuggguguauu caaggcuccu uuguuuaacu uuaagaagga gaccugcuaa caaugcugca    120
aggagccuug aauacaccaa ugaccaugau uacggauuca cuggccgucg uuuuacaacg     180
ucgugacugg gaaaacccug gcguuaccca acuuaaucgc cuugccgccc auccccuuu      240 cgccagcugc cguaauagcg aagaggcccg caccgaucgc ccuucccaac aguugcgcag    300
ccugaauggc gaauggcgcu uugccgcggc cgcacucgag uaagcaacua gcauaaccc     360 uuggggccuc uaaacggguc uugagggguu uuuug                                395
```

PAPER-BASED COLORIMETRIC COVID-19/SARS-COV-2 TEST

REFERENCE TO RELATED APPLICATIONS

This application is a U.S. non-provisional application claiming priority under 35 U.S.C. 120 and 119(e) to U.S. provisional application No. 63/024,295, filed May 13, 2020. The disclosure of this priority application is incorporated herein in its entirety.

FEDERALLY SPONSORED RESEARCH STATEMENT

This invention was made with government support under Grant Number 3U54HL143541-02S1 awarded by the National Institutes of Health. The government has certain rights in the invention.

BACKGROUND

The present disclosure relates to systems, kits, and methods useful for analyzing biological specimens. In particular, the present disclosure provides devices and methods utilizing RNA biosensors in the context of cell-free transcription/translation systems for analyzing samples potentially containing viral particles, particularly SARS-COV-2, the causative pathogen of the disease COVID-19.

The unprecedented impact of COVID-19 on the U.S. economy, education, mental health, food supply chain, health care availability, and probability of severe risk of disease or death is profound. One of the biggest challenges to stopping the spread of the virus is "silent transmission" through infected individuals who have yet to show symptoms during the up-to-14-day incubation period or through asymptomatic carriers, as studies estimate that up to 88% of infected people do not exhibit symptoms. The lack of a simple inexpensive diagnostic test for the virus impedes measurement of the masses, which measurement will allow health planners to properly coordinate public health response to predicted and current rates of infection.

Covid-19 disease hit the United States when the U.S. healthcare system was not prepared with adequate numbers of diagnostic tests to clearly identify infected persons. This slowed detection of hot spots and may have contributed to faster spread. Although the rate of infection has slowed recently, the vast majority of American have not been tested. Furthermore, testing for infection is not a one-time event, and ongoing testing can be beneficial, particularly in regions of high infection or suspected silent introduction. Indeed, spread by asymptomatic infection is a constant risk and "the Achilles heel of current strategies to control Covid-19." Moreover, the virus has also mutated into different forms that require further testing and monitoring.

Proper epidemiology modeling and healthcare response relies heavily on knowing the distributions of infected and non-infected persons. Yet testing everyone with conventional technology is slow and expensive. There is the possibility that such required testing may be needed for years until a successful vaccine is available or herd immunity is attained in the general population. In addition, without needed scientific and technological advances, future pandemics will face similar challenges.

BRIEF SUMMARY

In one aspect, the present disclosure provides a kit for detecting a target nucleic acid in a sample. The kit may include an in vitro coupled transcription-translation system, and a switch which may be at least one of (i) an RNA molecule capable of adopting a self-binding structure (a pseudoknot, a modified stem-loop, a loop-loop, and a RNA-IN/OUT structure); or (ii) a DNA molecule which can be transcribed to yield an RNA molecule capable of adopting a self-binding structure (a pseudoknot, a modified stem-loop, a loop-loop, and a RNA-IN/OUT structure). The switch may be inactive when adopting the self-binding structure, and active when annealed to the target nucleic acid. The in vitro coupled transcription-translation system and the switch may be disposed on a surface.

In another aspect, the present disclosure provides method of detecting a target nucleic acid in a sample. The method may include applying the sample to a surface of a kit. The kit may include an in vitro coupled transcription-translation system and a switch including at least one of: (i) an RNA molecule capable of adopting a self-binding structure (a pseudoknot, a modified stem-loop, a loop-loop, and a RNA-IN/OUT structure); or (ii) a DNA molecule which can be transcribed to yield an RNA molecule capable of adopting a self-binding structure (a pseudoknot, a modified stem-loop, a loop-loop, and a RNA-IN/OUT structure). The switch may be inactive when adopting the self-binding structure, and active when annealed to the target nucleic acid. The in vitro coupled transcription-translation system and the switch are disposed on the surface. The method may include analyzing a signal generated by a reporter.

BRIEF DESCRIPTION OF THE DRAWINGS

Reference is made to the following drawings, wherein:

FIG. 6 comprises FIGS. 6A-6B. FIG. 6A is a graph showing detection of a small molecule from a dehydrated cell free protein system;

FIG. 6B is a bar graph showing cell-free expression of a reporter protein in the present of various human sample matrices;

FIG. 10 comprises FIGS. 10A-10B. FIG. 10A is an image of disulfide bonds between viral capsid proteins; and FIG. 10B is a gel image illustrating breakdown of viral particles under reducing conditions similar to those of the cell-free environment according to the present disclosure.

DETAILED DESCRIPTION

Disclosed herein is a simple paper-based test (similar to a pregnancy test), that can be completed at home, rapidly be scaled to 300+ million tests to test everyone the country, and enable identification and quarantining of asymptomatic spreaders to more efficiently monitor and eventually eliminate spread of the disease. These tests could also facilitate daily testing by those who interact with high-risk individuals to prevent transmission and daily testing by high-risk individuals to catch the infection early and treat it early to prevent overwhelming our health care system and the limited number of ventilators available. Such a test would be invaluable in airports to quickly screen travelers, or for regular testing of patients and caregivers in care facilities or for children in schools. The key is a very inexpensive test that is simple, accurate, and easily scaled up for distribution.

Currently most diagnostic tests are PCR based, and require sending samples to clinical laboratories for testing on expensive diagnostic instruments, a process that takes 1-2 days, depending on the workflow at the clinical lab. In some cases, testing facilities can be overburdened, with waits increasing to five or more days before a result is communicated, and if the result is negative, a patient may not be contacted at all due to throughput and personnel constraints. Meanwhile patients who may be infected are sent home, potentially enhancing community spread of infection. A rapid at-home or point-of-care diagnosis will relieve stress on clinical laboratory resources and drive-through sampling clinics, reduce the need for face-to-face contact required with current tests, and relieve stress of some individuals who are anxious about going out to be tested or about whether they are infected.

Due to the long and variable latency period of COVID-19, the CDC has a disclaimer that early stage infection might not be detected; thus there is continuing anxiety even after a negative result. Thus, a mass produced low-cost sensor as described herein can enable potentially daily testing and reduce the documented negative psychological effects caused by the pandemic.

In one aspect, a test or method as described herein can employ a new RNA switch with high selectivity. In the context of shelf-stable cell-free protein synthesis reagents, RNA "toehold" switches may be used as a sensor for RNA molecules including viral RNA molecules. While the simple nature of the hairpin switch is a natural choice, it lacks the selectivity and has too high of a background signal to be employed in the clinical setting without first PCR amplification of RNA from the sample. Thus, there is no value added as it is more straightforward to use PCR alone for detection. There may also be issues with matrix effects from human samples.

The devices and methods of the present disclosure overcome these matrix effects as will be described later in the proposal using a different type of sensor that has the sensitivity for clinical relevance for cancer treatment and prevention of endocrine disruptor exposure. To overcome the RNA switch challenge, the device of the present disclosure employs a pseudoknot structure to increase the selectivity and minimize background signal issues found in the "toehold" switch.

Pseudoknot RNA has secondary structure which includes at least two stem-loop structures, in which a portion of one these stems is intercalated between the halves of another stem. Stems or other portions of the pseudoknot may cross each other and overlap once or multiple times. Pseudoknot structure is difficult, and sometimes impossible, to predict using software, even when the location of base-pairing stems are known.

In one aspect, a test of the present disclosure may be provided directly with RNA pseudoknot molecules combined into the cell-free extract. In another aspect, the test of the present disclosure may be provided with DNA molecule, such as a plasmid or a linear DNA molecule, which encodes the RNA pseudoknot. In such an aspect, the transcription machinery will engage the DNA template and generate the pseudoknot switch when the test is activated. The DNA construct can include regulatory elements, such as promoters, to assist in generation of pseudoknot RNA.

Figure 1:
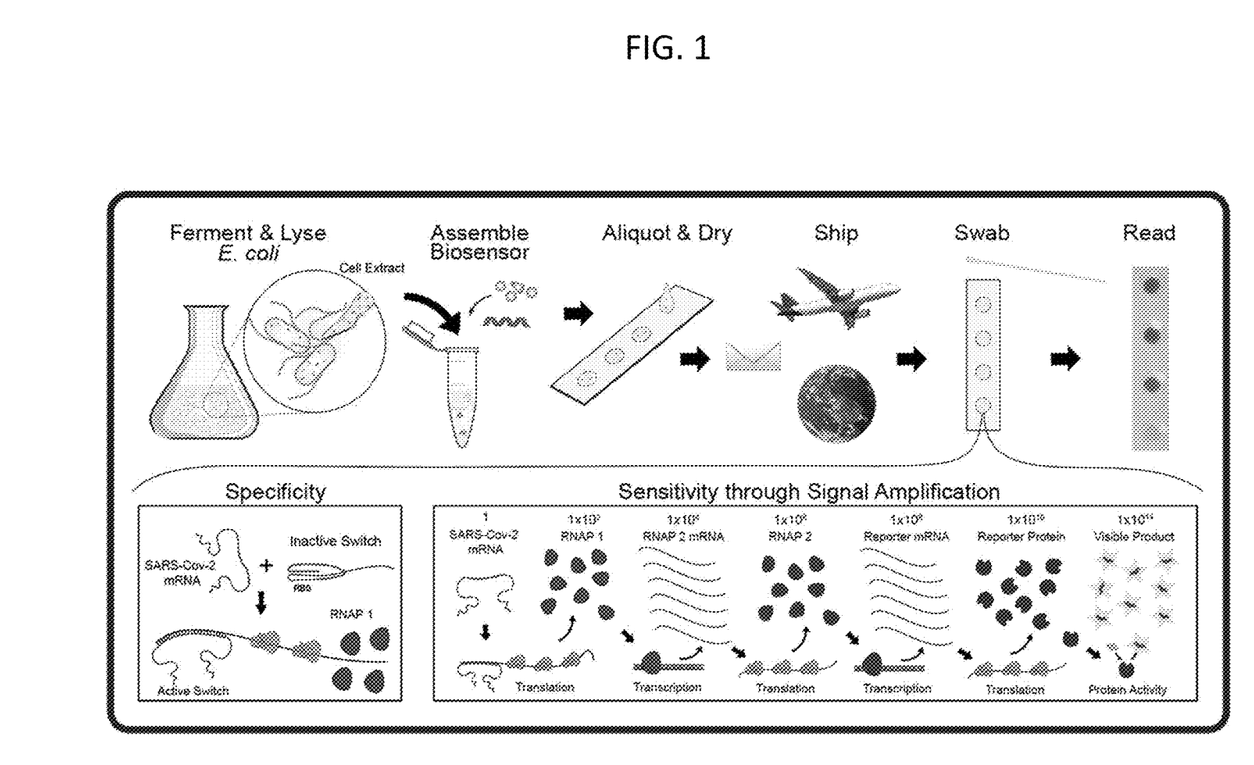
FIG. 1 provides schematic views of tests and methods according to the principles of the present disclosure.

FIG. 1 illustrates a proposed cell-free SARS-CoV-2 sensor's assembly, shipment, and at-home use. The "Specificity" box illustrates screening of pseudoknot RNA switch designs for selectivity. The "Sensitivity through Signal Amplification" box illustrates signal amplification by extra transcription and translation steps using multiple orthogonal RNA polymerases (RNAPs) such that the signal could be conservatively amplified by $10^{14}$. Under "Read" is a photograph of a paper sensor with dried cell-free reagents subsequently hydrated and illustrates a readout from a SARS-CoV-2 sensor (top 3 color readouts are for each of the 3 CDC-specified SARS-CoV-2 mRNA detection sequences and the bottom spot is a control to verify test accuracy). Only 15 µL of reagents are used in each visible spot and the very low volumes of reagents required greatly reduces the cost and simplifies mass production. Lipase and protease expression in *E. coli* is provided during the first "Ferment" step, such that the enzymes would be present in the biosensor reagents to break apart SARS-CoV-2 capsid and make more RNA available for higher test sensitivity.

The sensors disclosed herein apply not just transcription level amplification, but a cascade of transcription-translation signal amplification by using multiple orthogonal RNA polymerases in series. This will eliminate the need for PCR amplification for clinically relevant detection of viral genomic RNA.

Viral RNA accessibility to the sensor also represents a challenge. Viruses have been evolutionarily selected for enhanced stability on surfaces, and then they disassemble inside cells to enable infection. The cell-free environment of the presently disclosed sensors contains reductases from cell cytoplasm that keep the environment reducing and this environment breaks and prevents the reformation of disulfide bonds, greatly weakening the stability of viral coat proteins. Thus, the native sensor environment will help destabilize the virus. To further enhance disassembly of the virus for genomic RNA availability, detergents, lipases, and proteases can be recombinantly or exogenously supplied and balanced against negative effects (degradation/inhibition of reporter enzyme and potentially slower cell growth during recombinant expression). Because the cell-free protein synthesis environment does not need a cell wall for function, detergents can be included. This will allow the sensor to detect not only free genomic RNA material but the RNA inside assembled viruses.

The test kit disclosed herein can be scaled up to provide a simple paper-based test that can be done at home at very low cost in 30 minutes. The kit includes a "cell-free" in vitro protein-synthesis-based test that enables engineering of life molecules for highly specific sensing, but in an in vitro format with shelf-stable reagents dried on paper. The "cell-free" format uses transcription and translation machinery easily harvested from *E. coli* (FIG. 1) which can be activated in the presence of a unique substrate without interfering cell wall. This open environment allows for mixing highly specific biological sensors directly in sample matrices to enable single molecular signal amplification through transcription and translation. In addition, the dried, shelf-stable cell-free reagents are sterile and can be prepared in a safe "endotoxin-free" format. Cell-free reagents have also been shown to operate with identical kinetics at the micro liter up to the 100-liter production scale, which simplifies scale up for mass production and provides confidence in identical performance of each microliter aliquot that make up each test.

The approach is also well suited to the current pandemic due to its ability to work in possible sample matrices including oropharyngeal mucus, saliva, stool, blood, and urine. The just-add-sample format requiring only 30 minutes for a distinct colorimetric response makes it easy for at-home or point-of-care use, and the low cost enables daily (even hourly) testing if needed. Scale-up manufacturing is simplified as each test requires microliters of reagents that are straightforward to prepare and need only be dropped onto paper and dried.

The testing devices and methods disclosed herein have greater selectivity compared to current "toehold RNA switches," which lack selectivity and low background signals), sensitivity (as clinically relevant levels are currently undetectable without external signal amplification steps), and viral RNA access (to detect very low viral loads, disassembly of the virus so as to detect its genome is essential).

Figure 2:
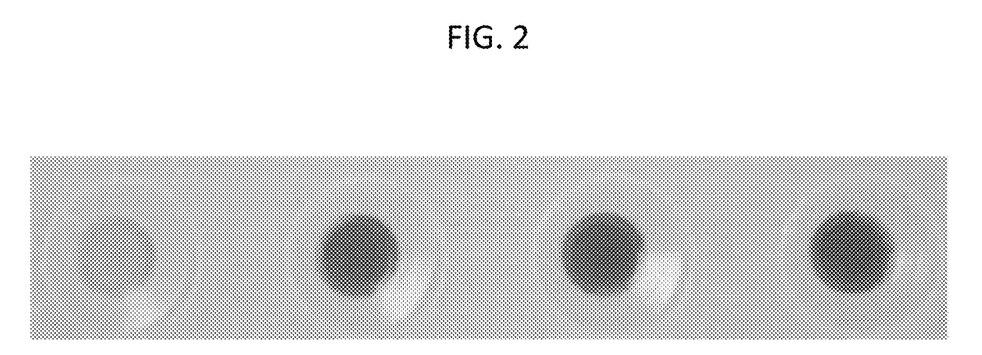
FIG. 2 is a photograph of a test surface using a biosensor similar to those described herein.

The present devices can make use of different paper types for support of cell-free biosensor. FIG. 2 illustrates results of cell-free biosensing from 15 μL of dried reagents of 3 different paper types. Tests of the present disclosure may include cell free extracts including transcription/translation systems and the pseudoknot RNA or RNA precursor dried and spotted on a surface, such as a paper surface. The paper surface can be selected from paper materials including, but not limited to, cellulose acetate, chromatography paper, printer paper, ashless filter paper, and other cellulose-containing materials (such as bath tissue and paper towel). In another aspect, the test can include a cell-free extract spotted and dried onto surfaces including those defined by polymers (polypropylene, polyethylene, and so forth), glass, and metal (aluminum, tin, and so forth).

In one aspect, the present test requires no extra equipment, so that it can be conducted outside of a laboratory setting. The test can be easily mass-produced with minimal reagent costs. The technology is built upon cell-free protein synthesis biosensors which repurpose biological machinery harvested from one of the least expensive sources, E. coli. The test device of the present disclosure has good reagent stability, overcomes inhibitory effects in human samples, uses safe reagents, and detects virus at clinically relevant concentrations. Detecting a single viral RNA genome per microliter of sample as the devices and methods of the present disclosure are able to do requires exquisite selectivity, sensitivity, and signal amplification.

Conventional toehold RNA switches which have been used for cell-free biosensing of viral genomic RNA suffer from low sensitivity and require a sample amplification step to approach clinical relevance. This amplification step requires extra equipment and reagents and adds about three hours to the assay duration. Such a format does not facilitate universal, economic distribution and rapid, point-of-care testing basis for low sensor sensitivity is leaky translation initiation from the RNA switch in the OFF 3' conformation. In other words, the structural free energy of RNA switch transcript remains too high to effectively repress translation initiation and enable sensitive detection. RNA switches employing pseudoknot secondary structure as a regulator of protein translation to enable sensitive detection of viral RNA.

Figure 3:
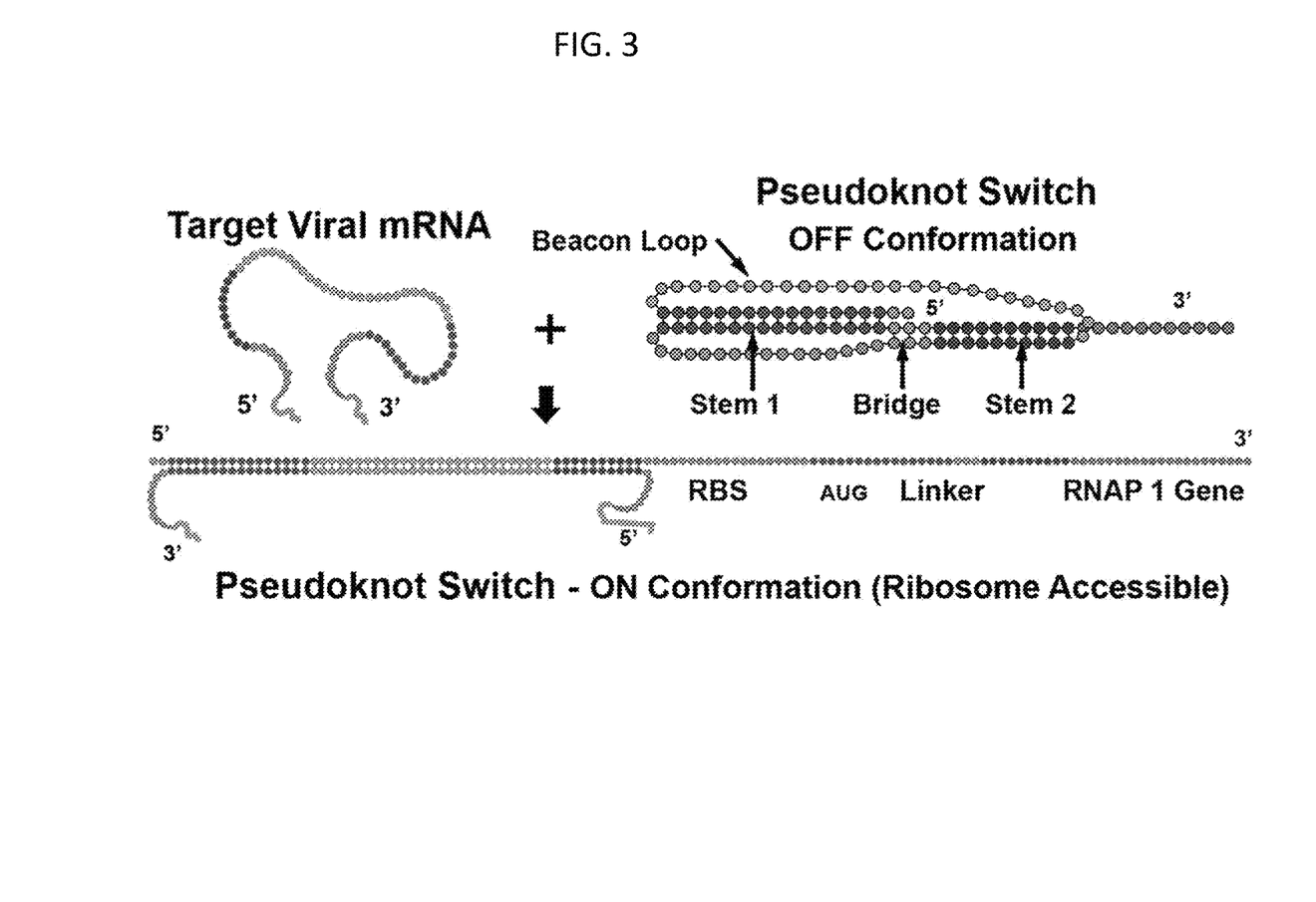
FIG. 3 is a schematic view of an RNA pseudoknot switch.

FIG. 3 illustrates the pseudoknot switch, which features stiff steric hindrance to ribosome binding in OFF confirmation and open conformation in the ON confirmation. In the OFF state, the pseudoknot design enables a very stable equilibrium structure including two, tight loops that flank two stems. The ribosome binding site (RBS) is pinched by these stems, essentially tied in a "knot" which restricts its freedom and accessibility to the ribosome. Stem 1 sequesters the start codon and the spacer region between start codon and the RBS Shine-Dalgarno sequence. The resulting structure effectively represses translation initiation because the 30S ribosomal subunit spans the Shine Dalgarno and start codon sequences during successful translation initiation. Furthermore, the pseudoknot structure tightens the ribosome binding site in close proximity to the double-helix structure of Stem 1, preventing ribosome binding with stiff steric hindrance. Stem 2 of the pseudoknot structure forms upstream of the ribosome binding site and tightens the recognition loop, again creating steric hindrance to interactions with the ribosome. This results in strong inhibition of translation initiation.

Figure 4:
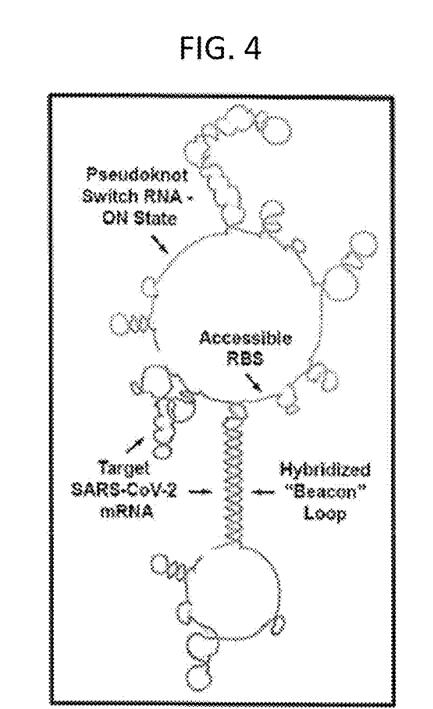
FIG. 4 is another view of an RNA pseudoknot switch according to the principles of the present disclosure.

Repression of translation initiation is removed by energetically favorable base pairing of the RNA switch transcript with the target RNA molecule to create an ON conformation (FIG. 3). This is enabled by the recognition or "beacon" loop which is complementary to the target viral RNA molecule. After the beacon loop hybridizes with the viral RNA target, both stems of the pseudoknot, which are also complementary to the target viral RNA molecule, are melted by branch migration. In one respect this may be thought of as "toehold-mediated strand displacement" of both stem 1 and stem 2, and the formation of a highly energetically favorable RNA duplex. This transformation converts the pseudoknot into an open RNA structure that highly favors translation initiation as predicted by NUPACK simulation (FIG. 4). In the presence of the target viral sequence, the free energy of the ON conformation is calculated by NUPACK as −32 kcal/mol than that of the solitary switch in the OFF conformation (FIG. 4).

FIG. 4. NUPACK analysis of SARS-CoV-2 target mRNA in "ON" conformation complex with pseudoknot switch RNA. Depicted switch forms an energetically favorable double-helix 60 nucleotides in length.

Figure 5A:
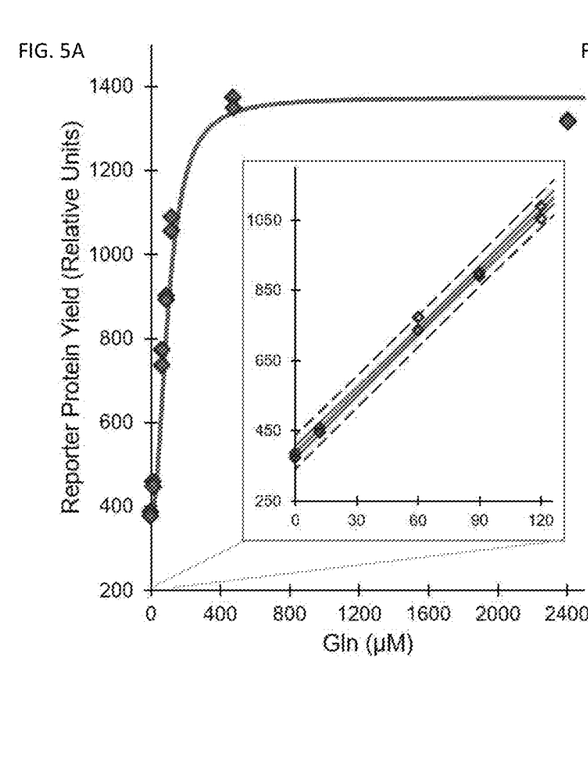
FIGS. 5A-5C are a series of graphs showing efficacy of detection of a target using a test based on a cell-free transcription/translation system.
Figure 5B:
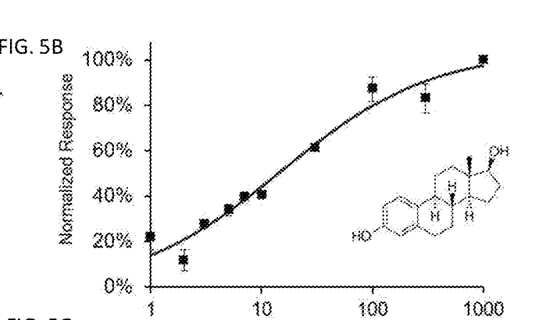
Figure 5C:
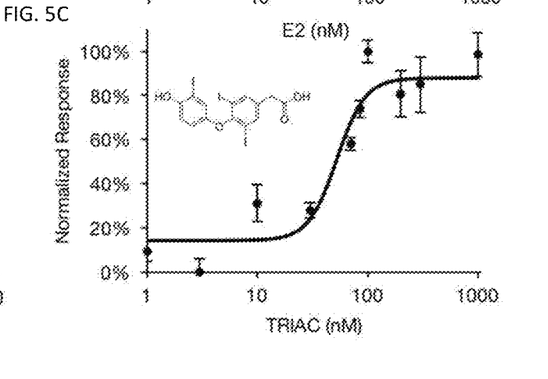

Cell-free protein synthesis-based biosensors are versatile and can aid in testing a variety of different compounds including small molecule endocrine disrupting chemicals and translation-dependent amino acid concentrations (FIG. 5). FIG. 5 illustrates (A) Cell-free detection of L-glutamine in human blood serum; (B) cell-free detection of estradiol (E2) in urine; and (C) Cell-free detection of thyroid hormone tiratricol (TRIAC) in raw sewage. The open in vitro cell-free environment enables direct control of additive concentrations and rapid screening, such as in a glutamine sensor (a target of metabolic cancer treatment approaches in phase II clinical trials) to clinically relevant concentrations (FIG. 5).

Figures 6, 6A, 6B:
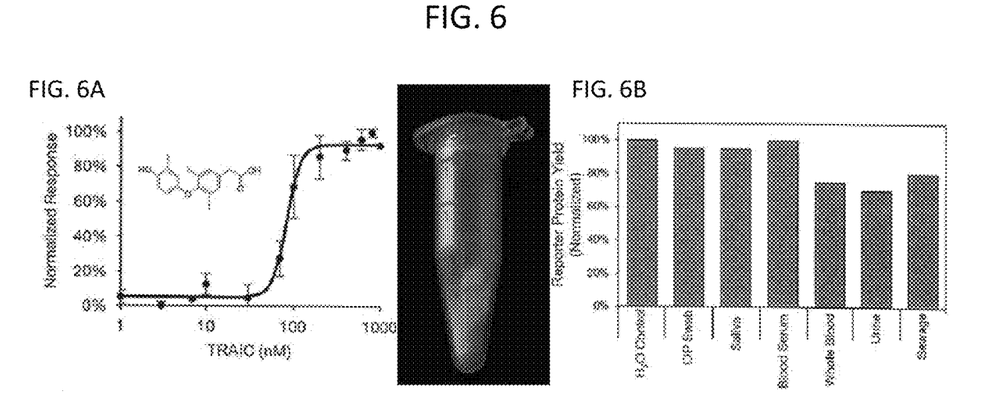

Tests and methods of the present disclosure can use pseudoknot RNA switches for all 3 sequences recommended by the CDC for SARS-CoV-2 detection using the design methodology below We have demonstrated ability of our cell-free biosensors to function from shelf-stable lyophilized/dried reagents (FIG. 6), and in human blood, human urine, and raw sewage samples, in which small molecules or metabolites are the target. FIG. 6 illustrates (A) a cell-free detection of tiratricol (TRIAC) from dehydrated CFPS components, and (B) cell-free expression of reporter protein in the presence of human sample matrices. More recent results demonstrate that the cell-free protein synthesis reaction that drives the biosensor functions well in oropharyngeal and spittle samples through the use of an RNAse inhibitor to maintain high activity in samples from different individuals (FIG. 6).

Pseudoknot RNA Switch Design for Translation Regulation

Pseudoknot switch design was guided by RNA secondary structure predictions using NUPACK and components in pseudoknot NMR structure determinations. Because most structure prediction algorithms are blind to pseudoknots, predictions were made using two and three RNA molecules to represent components of the pseudoknot. The virtue of the pseudoknot design is the steric hindrance to ribosome binding and low free energy of the equilibrium structure, yet, stems which are too long prevent effective branch migration.

Pseudoknot switches can have a variety of lengths of the 1) beacon loop, 2) stem 1, 3) stem 2, and 4) bridge sequences (FIG. 3). All four components can be modified independently to create a library of functioning RNA switch designs, which can function in an experimental screen to report the effectiveness of a design with the sensitivity and low background signal levels to enable the proposed SARS-CoV-2 test.

Pseudoknot RNA Switch Screening

A high-throughput cell-free system as disclosed herein can use linear DNA from PCR products as a template. Thus, variations to the designs can be created and assessed in hours. PCR and linear DNA can be used to rapidly screen product variants. A pseudoknot construct with the selectivity necessary for the proposed SARS-CoV-2 can be designed by doing so and the design of other cell-free pseudoknot sensors for RNA targets against other diseases.

The pseudoknot RNA switch may target RNA sequences with homologies ranging from 80 to 99% of the SARS-CoV-2 sequence, or 99% or greater selectivity. The pseudoknot design can be employed as a transcriptional RNA switch regulator. Its demonstrated tight binding can facilitate a strong off signal, which is a compelling approach to overcome currently used toehold switches. Alternative switch designs may also be used in tests and methods of the present disclosure, including but not limited to modified stem-loop, loop-loop, and RNA-IN/OUT structures which also have structural free energies to maintain a strong "off" signal.

Other candidate switches can be identified by employing a high throughput screen. The present disclosure contemplates the modification and use of a toehold switch construct. Examples of modifications may include lengthening the hybridized secondary structure, increase the GC content of the secondary structure and shorten the toehold sequences to reduce or eliminate leaky expression from this sensor construct. Expression of the sensor construct will be performed prior to drying the biosensor reagents such that the construct will be synthesized throughout the test time and a high initial concentration will be available to facilitate the identification of 1 genome of viral RNA per microliter of sample. The sensor construct will also be produced by an endogenous RNA polymerase promoter during cell fermentation such that the extract used as a primary reagent for the cell-free biosensor should contain a significant concentration of this sensor mRNA.

In one aspect, the target to be investigated will have a sequence according to SEQ ID NO. 1: 5'-ggagccttgaatacaccaaaagatcacattggcaccgcaatcctgctaacaatgctgca-3'. In such an aspect, the pseudoknot switch may be transcribed by a DNA having a sequence similar to or identical to SEQ ID NO. 2: 5'-TAATACGACTCACTATAGGtgcagcattgttagcaggattgcgggtgccaatgtgatcttttggtgtattcaaggctccTT TGTT-TAACTTTAAGAAGGAGAcctgctaacaatgctgcaaggagcctt-gaatacaccaATGACCATGATTA CGGATTCACTGGCCGTCGTTTTA-CAACGTCGTGACTGGGAAAACCCTGGCGTTACCC AACTTAATCGCCTTGCCGCC-CATCCCCCTTTCGCCAGCTGGCGTAATAGCGAAG-AGG CCCGCACCGATCGCCCTTCCCAACAGTTGC-GCAGCCTGAATGGCGAATGGCGCTTTG CCGCGGCCGCACTCGAGTAAGCAACTAGCAT-AACCCCTTGGGGCCTCTAAACGGGT CTTGAGGG-GTTTTTTG-3'. The features of this pseudoknot sequence will be described with regard to FIG. 7.

The RNA sequence of a resulting pseudoknot from the DNA is as follows, in SEQ ID NO. 3: 5'-UAAUACGACU-CACUAUAGGugcagcauuguuagcaggauugcgggugccaau-gugaucuuuugguguauuca aggcuccuuuGuuuAACUUUAA-GAAGGAGAccugcuaacaaugcugcaaggagccuugaauacac-caAUGA CCAUGAuuACGGAuuCACuGGCCGu-CGuuuuACAACGuCGUGACUGGGAAAACCCUGG CGUUACCCAACUUAAUCGCCUUGCCGCC-CAUCCCCCUUUCGCCAGCUGGCGUAAU AGCGAAGAGGCCCGCACCGAUCGCCCUUCC-CAACAGUUGCGCAGCCUGAAUGGCG AAUGGCGC-UUUGCCGCGGCCGCACUCGAGUAAGCAACUAG-CAUAACCCCUUGGGG CCUCUAAACGGGUCUUGAGGGGUUUUUUG-3'.

Figure 7:
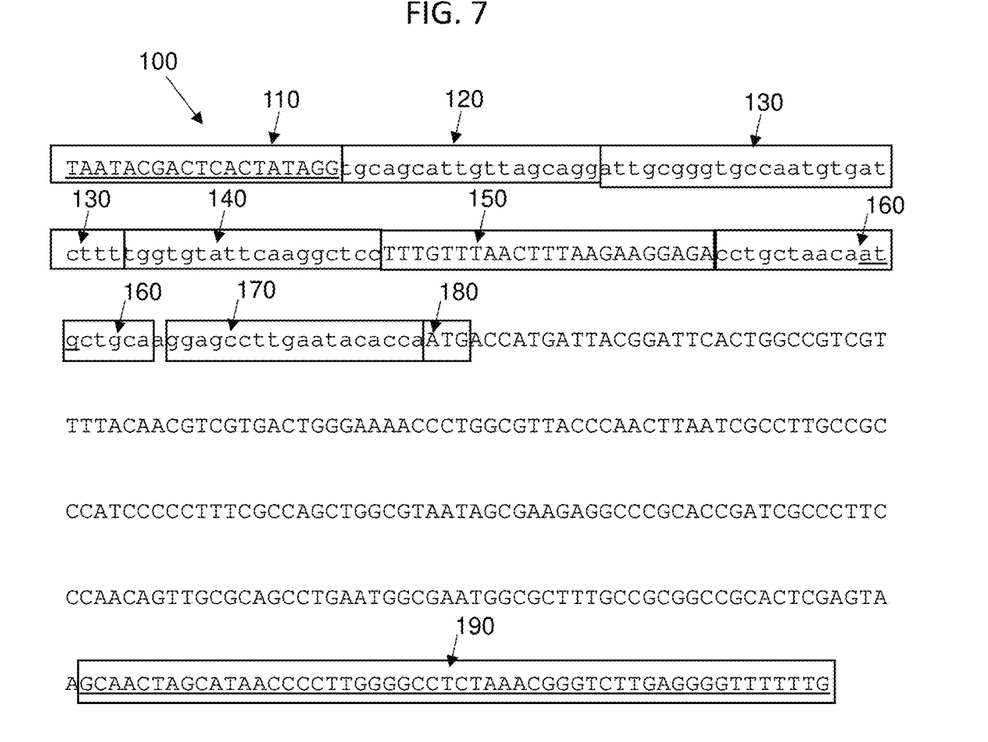
FIG. 7 illustrates the sequence components of a pseudoknot structure in accordance with the principles of the present disclosure.

FIG. 7 illustrates a DNA sequence 100 which may be transcribed to define an RNA pseudoknot, and is SEQ ID NO: 2. The pseudoknot defined by sequence 100 targets an RNA of sequence SEQ ID NO: 1. The sequence in box 110 is a T7 RNA polymerase promoter sequence, and the sequence in box 190 is a T7 terminator sequence. If a different RNA polymerase is to be used, these sequences may be swapped for corresponding promoter and terminator elements.

The sequence in FIG. 7 is illustrated in the conventional 5' to 3' direction. The sequences in boxes 120, 130, and 140 together represent sequence that is complementary to SEQ ID NO: 1. When the pseudoknot is in its ON or open configuration, this stretch of nucleotides will bind to SEQ ID NO: 1, which is a portion of the SARS-COV-2 genome. The sequence in box 160 has sufficient complementarity to that in box 110, and that in box 170 has complementarity to the sequence in box 130, to bind and sequester these sequences when the target sequence is absent. This keeps the pseudoknot in the OFF or self-bound configuration. The sequence in box 180 is a start codon for a reporter protein, such as the alpha complement of beta-galactosidase, as illustrated. A person of ordinary skill in the art will appreciate that another reporter may be used instead, particularly the alternatives disclosed herein.

Signal Amplification

As an energy efficient control system, life naturally reuses DNA for transcription and RNA for translation many times with significant amplification at each transcription or translation event. Current cell-free biosensors for RNA detection only take advantage of a single translation event for their signal amplification (~$10^2$ amplification) and thus require PCR to obtain $10^6$ (25 cycles) to $10^9$ (30 cycles) amplification before the system is sensitive enough to detect a high viral load. To obtain the very low level of detection proposed of 1 genome unit per microliter or $10^{-17}$ M, signal amplification of $10^{14}$. This $10^{14}$ amplification can be obtained through a translation/transcription cascade capped off by enzyme activity amplification as illustrated in FIG. 1. The cascade operates downstream of the RNA switch with mutually orthogonal T7 and T3 RNA polymerases. The initial RNA polymerase synthesized from the RNA switch may carry an N-terminal linker as a result of the switch design; however, bacteriophage RNA polymerases have been shown to function well with larger N-terminal tags. In one aspect, the reporter enzyme to be used may be β-galactosidase as it has demonstrated successful use as a colorimetric cell-free biosensor reporter. In another aspect, the reporter may be a lactamase, such as beta-lactamase; a luminescent enzyme, such as a luciferase or luciferase variant; a fluorescent protein, such as green fluorescent protein; or chitinase.

Figure 8:
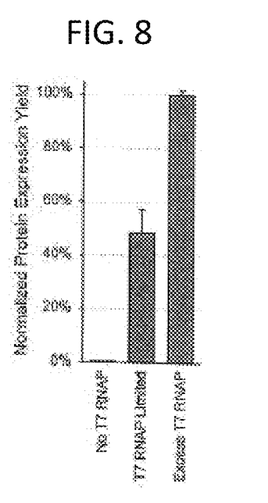
FIG. 8 is a bar graph illustrating cell-free transcription/translation yields with varying concentrations of T7 RNA polymerase.

In a cell-free synthesis system, protein yields may be directly proportional to the DNA template concentration added (transcription), the RNA polymerase concentration, and the mRNA concentration levels (see FIG. 8, which illustrates cell-free transcription/translation yields with varying T7 RNAP concentrations.) T7 and T3 RNA polymerases work orthogonally in the *E. coli*-based cell-free system for the described biosensor. These RNA polymerases can be used in concert in this cell-free system as polymerases to synthesize each other in a cell-free biosensing system. Transcription by T7 RNA polymerase, translation of the proposed reporter protein, and reporter protein activity all perform well in the present cell-free biosensing environment and in the presence of human sample backgrounds. T3 RNA polymerase also functions at the same level of T7 RNA polymerase in this cell-free protein synthesis system, which is capable of expression of multiple expression constructs in our cell-free system and optimized the recombinant of expression of multiple different exogenous components (such as the T7 and T3 RNA polymerases) for function in the cell-free system.

The cell-free extract systems as described herein can be derived from a number of different cell types. Extracts from prokaryotic, eukaryotic, and archaeal cells can be utilized in in such a system. In one aspect, the cell can be a bacterial cell, such as a cell from *E. coli*. In another aspect, the cell can be a eukaryotic cell, such as an *S. cerevisiae* cell, or a mammalian cell, such as a human erythrocyte.

The cell-free system can amplify signal by creating cascading transcription/translation series (thereby defining a cell-free transcription/translation system), to enable detection of a single viral RNA genome from SARS-CoV-2 per microliter of sample.

Although reference is made herein to testing for COVID-19 and SARS-CoV-2, it will be appreciated that tests and methods as disclosed herein can be applied to a great variety of diseases and conditions. For instance, other coronavirus can be tested with similar RNA switches, such as SARS and MERS; or other viruses, including Zika, dengue, influenza, common cold (inclusive of any rhinovirus), hepatitis (including hepatitis C and E), poliovirus. Other conditions can be tested for with similar systems and tests, such as mumps and measles.

Prior to the present disclosure, transcription and translation cascades were not engineered into cell-free systems. Such a system may use the orthogonal T7 and T3 RNA polymerases, but different orthogonal polymerases may be employed as desired. RNA switch constructs with either T7 and T3 as the initial RNA polymerase will be compared in their ability to tolerate an N-terminal tag and quickly initiate the cascade with minimal background expression. In one aspect, SP6 bacteriophage RNA polymerase may be used instead of, or in addition to, one of T7 and T3 polymerase. Although two different RNA polymerases are shown in FIG. 1 to obtain the signal amplification desired, these amplification numbers are conservative estimates and signal series that contain only 1 RNA polymerase will also be assessed relative to orthogonal RNA polymerases. This modification may further shorten the time needed between applying the sample to the sensor and reliable readout. The cell-free biosensors can provide a reliable readout in as little as 90 minutes, or 60 minutes, or 30 minutes, or 15 minutes. In some cases, the endogenous polymerases may be used to produce the initial sensor mRNA.

The cell-free approach lacks a cell wall and enables direct control of DNA template concentrations added to the reaction environment. Higher DNA template concentrations may be used for the most downstream portions of the cascade. Template concentrations for use in the cell-free system for the expression of multiple different proteins simultaneously from different constructs can be determined by a person of skill in the art. Differences in RNA secondary structure may play a role in varying expression ratios different than the DNA concentration ratios. A feature of cell-free biosensors is that sensor template concentrations can be quickly and efficiently changed and intermediate protein concentrations directly compared by directly adding a radiolabeled amino acid and then SDS-PAGE, autoradiography, and densitometry.

In some instances, RNA polymerases may not retain the high level of orthogonality as reported in literature. Fortunately, a wide variety of orthogonal RNA polymerases have been engineered that function in the present *E. coli* based system and other polymerases can be employed therein. In some aspects, the large number of additional transcription and translation steps beyond the single step of the originally tested RNA sensor could extend the time the test needs to incubate before a reliable signal is available. Given the rapid speed of the viral polymerases proposed for transcription and translation machinery in *E. coli*, this is a less likely event; however, reducing the number of amplification steps can accelerate the test. Additionally, *E. coli*-based cell-free transcription and translation machinery operate with the highest kinetics at human body temperature, and the patient can hold a plastic-wrapped test in his hand or against his body to reduce the time needed before readout.

Figure 9:
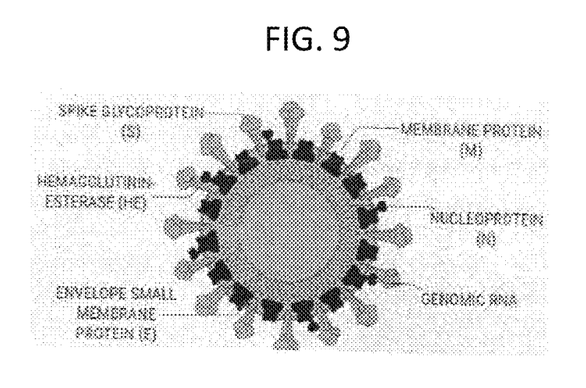
FIG. 9 is a cross-sectional diagram of a viral particle.

In Situ Viral Disassembly for Enhanced Viral RNA Availability and Test Sensitivity A natural reducing environment of detergents, lipases, and proteases can be included in the presently disclosed cell-free biosensor to facilitate SARS-CoV-2 disassembly and make available more SARS-CoV-2 RNA for enhanced test sensitivity. SARS-CoV-2, like most viruses, has evolved to protect its genomic material as long as possible to improve the odds of infecting a new host. Part of that protection includes disulfide-bonded proteins, a lipid coat, and a protein coat, with an illustration of the structure, including outer membrane and nucleocapsid shown in FIG. 9. The present devices and methods seek to break apart both the lipid and protein coats to better release the viral genome for more interaction with the SARS-CoV-2 test reagents. Beyond the test disclosed, better understanding of conditions which disassemble the virus could be useful in cleaning surfaces against the virus that are sensitive to traditional cleaning supplies (e.g. bleach, ethanol).

Figures 10, 10A, 10B:
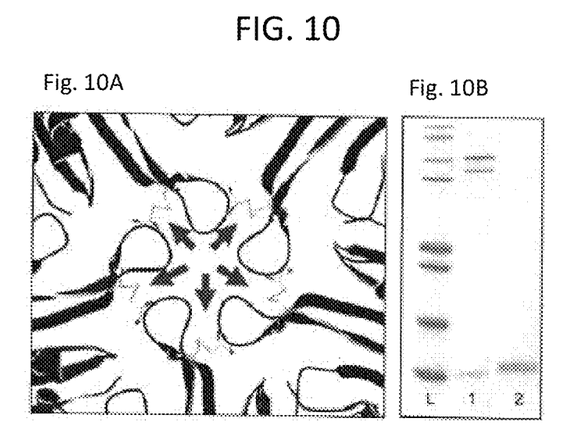

The cell-free environment is kept in reducing state due to active reductases that are included in the cell-free environment as part of the *E. coli* lysate. This reducing state breaks virus capsid disulfide bonds (FIG. 10). FIG. 10A is an image of disulfide bonds between Qβ viral capsid proteins, including a protein gel of assembled Qβ capsid proteins under oxidizing conditions or the reducing conditions equivalent to the redox-potential of the cell-free environment that causes 5- and 6-mer disulfide bond breakage and capsid proteins monomerized (FIG. 10B). L is a reference protein ladder.

Exogenous proteins can be produced while fermenting the E. coli cells that are then lysed to provide the machinery for cell-free biosensors. Detergents such as Tween and polyethylene glycol can be added while maintaining the cell-free environment. While protease deficient E. coli BL21 strains work well, strains that maintain elevated concentration of Lon and OmpT proteases are also viable; thus including protease production at lower concentrations is a viable approach. Finally, the E. coli cell wall is removed from the cell-free environment prior to use as a biosensor, such that lipase and lysozyme enzymes which break apart cell walls and viral membrane coats can be included in the cell-free system without inhibiting transcription and translation. Combining lipase, protease, detergent, and redox conditions can enable greater than 20% disassembly of SARS-CoV-2 capsid while the cell-free SARS-CoV-2 test is occurring.

Accessibility of RNA from SARS-CoV-2 can be assessed by PCR after treatment with lipases, proteases, and detergent at the redox potential maintained in the cell-free reaction. An aliquot of a sample having a known amount of SARS-CoV-2 can be tested by quantitative reverse transcription PCR (RT-qPCR) to determine accessibility of the 3 RNA sequences specified for SARS-CoV-2 detection by the CDC. The samples can then be assessed for viral RNA accessibility by RT-qPCR after disassembly conditions created by exposure to varying concentrations of lipases, proteases, and detergents in a disulfide-bond reducing environment. Initially lipases used in laundry detergents and those excreted by pathogenic bacteria and fungus or in wasp venom can be employed due to their known ability to break down the human membrane that comprises SARS-CoV-2 outer shell (including alkaline yeast lipase, phospholipase A, lysophospholipase). In addition, detergents that do not inhibit transcription and translation in this cell-free environment, such as Tween, may also be included. General bacterial proteases such as OmpT and Lon and commercially available proteases used in laundry detergent may be used to break down the nucleocapsid protein (N protein). Once lipases and detergents have removed the outer membrane, the N protein may dissociate into the naturally 20-fold diluted cell-free environment and make the RNA more accessible for switch activation.

The lipase, protease, and detergent components can be added directly to the cell-free test environment, providing minimal inhibition of the transcription and translation sequence to detect SARS-CoV-2 genomic RNA. For ease in mass production, recombinant expression in E. coli during extract preparation during or following induction and growth procedures. Heterologous expression for cell-free systems may be conducted with the ClearColi "endotoxin-free" strain of BL21 E. coli such that there is minimal risk to users even if the test was accidentally consumed. Fortunately, a reducing environment is present and tolerates the detergents well. Furthermore, if coexpression of the lipases and proteases at concentrations as desired is challenging, these can be produced, purified, and directly added into the reagents outside of extract preparation. The increase in cost would be minimal due to the small volumes of reagents need per each test.

Extracts and detergents can be combined with the RNA switch sensor. Diagnostic tests can be spotted and dried on paper and challenged with decreasing RNA concentrations in buffer, in reconstituted porcine mucus, and in human nasal mucus. The sensor is able to detect SARS-CoV-2 down to 1 genome per microliter against SARS-CoV-2 virus included in human samples wherein at least 20% of the virus should be disassembled.

Although lipases, detergents, proteases, and a reducing environment should disassemble the virus, studies applying this biological approach to SARS-CoV-2 disassembly are very limited. In some cases, samples can be first heated up to high temperatures (~90° C.) before being applied to the test matrix. This could be done with a simple chemical heat pack. Another approach is to spread the sample on one side of a folded piece of paper that contains very high concentrations of lipase and proteases to facilitate higher disassembly before folding the paper in half to combine the RNA from the disassembled virus to the cell-free reagents that then detect the presence of the virus.

The test as disclosed herein may be supplied as a kit for home use or for laboratory use. The kit may include the test itself, which may include a card having the cell-free system spotted on a surface thereof. The spots may be designated by a border providing a visual indication of where to place the sample to be tested. The test may be stable for up to 30 days at room temperature, or up to 45 days, or up to 60 days, or up to 90 days, or up to 120 days, or up to 180 days, or up to one year. The kit may further include such materials as an instruction sheet, a swab, a chemical heat pack, and so forth.

A patient may collect his own sample and self-administer the test. The sample may be any of saliva, mucus, spittle, blood, and so forth. The patient collects a specified amount of the sample and places it on one or more designated testing zones of the test, portions of the surface on which the cell-free system has been spotted and dried. The patient then allows the test to incubate, optionally adding heat if instructed, and watches for the development of a signal from the reporter, such as a color change, to indicate a positive or a negative result. In some instances, a negative test will yield no change, whereas a positive test will yield a color change. In some instances there will be multiple testing zones on the surface of the test, and only one need report a positive to yield a presumptive positive result, provided that the control spot also develops.

While a limited number of aspects have been described, those skilled in the art, having benefit of the above description, will appreciate that other aspects may be devised which do not depart from the scope of the present disclosure. In addition, it should be noted that the language used in the specification has been principally selected for readability and instructional purposes, and may not have been selected to delineate or circumscribe the subject matter. Accordingly, the present disclosure is intended to be illustrative, but not limiting, of the scope of its contents.

The invention claimed is:

1. A kit for detecting a target nucleic acid in a sample, the kit comprising:
an in vitro coupled transcription-translation system; and
a switch comprising at least one of:
(i) an RNA molecule capable of adopting a self-binding structure comprising a pseudoknot; or
(ii) a DNA molecule, having SEQ ID NO: 2, which can be transcribed to yield an RNA molecule capable of adopting a self-binding structure comprising a pseudoknot;
wherein the switch is inactive when adopting the self-binding structure, and active when annealed to the target nucleic acid;
wherein the in vitro coupled transcription-translation system and the switch are disposed on a surface; and
wherein the RNA molecule binds SARS-Cov-2 messenger RNA.

2. The kit of claim 1, wherein the pseudoknot comprises at least two stem-loop structures in which a portion of one of the stem-loop structures is intercalated between the halves of another of the stem-loop structures.

3. The kit of claim 1, wherein when the sample is added to the surface, the in vitro coupled transcription-translation system comprises a reducing environment.

4. The kit of claim 1, wherein the in vitro coupled transcription-translation system and the switch are dehydrated and dried to the surface.

5. The kit of claim 1, wherein the surface comprises paper.

6. The kit of claim 1, wherein the kit is capable of detecting one viral genome per microliter of the sample.

7. The kit of claim 1, wherein the kit further comprises a signal amplification system.

8. The kit of claim 7, wherein the signal amplification system comprises nucleic acid for the expression of at least one of T7 RNA polymerase and T3 RNA polymerase.

9. A method of detecting a target nucleic acid in a sample, comprising:
applying the sample to a surface of a kit, the kit comprising:
an in vitro coupled transcription-translation system;
a switch comprising at least one of:
(i) an RNA molecule capable of adopting a self-binding structure comprising a pseudoknot; or
(ii) a DNA molecule, having SEQ ID NO: 2, which can be transcribed to yield an RNA molecule capable of adopting a self-binding structure comprising a pseudoknot;
wherein the switch is inactive when adopting the self-binding structure, and active when annealed to the target nucleic acid;
wherein the in vitro coupled transcription-translation system and the switch are disposed on the surface; and
wherein the RNA molecule binds SARS-Cov-2 messenger RNA.

10. The method of claim 9, wherein the sample is selected from oropharyngeal mucus, saliva, stool, blood, and urine.

11. The method of claim 9, wherein the pseudoknot comprises at least two step-loop structures in which a portion of one of the stem-loop structures is intercalated between the halves of another of the stem-loop structures.

12. The method of claim 9, wherein the kit tests for three sequences of SARS-Cov-2 messenger RNA.

13. The method of claim 9, wherein when the sample is added to the surface, the in vitro coupled transcription-translation system comprises a reducing environment.

14. The method of claim 9, wherein the in vitro coupled transcription-translation system and the switch are dehydrated and dried to the surface.

15. The method of claim 9, wherein the surface comprises paper.

16. The method of claim 9, wherein the kit is capable of detecting one viral genome per microliter of the sample.

17. A DNA molecule comprising SEQ ID NO: 2.

18. The method of claim 9, further comprising analyzing a signal generated by a reporter wherein the reporter is encoded by the RNA molecule and located downstream of the self-binding structure comprising a pseudoknot.

* * * * *